US012128191B2

(12) United States Patent
O'Brien et al.

(10) Patent No.: US 12,128,191 B2
(45) Date of Patent: Oct. 29, 2024

(54) MEDICAL DEVICE PACKAGE WITH A TWIST CAP

(71) Applicant: Hollister Incorporated, Libertyville, IL (US)

(72) Inventors: Daniel E. O'Brien, Calry (IE); Vincent Naughton, Sligo (IE); Martin McMenamin, Lifford (IE); Joseph N. Hanley, Sligo (IE); David A. Knauz, Riverwoods, IL (US); Martin P. Creaven, Ballina (IE); Stephen Collum, Castlebar (IE); Jeanne E. Lee, Libertyville, IL (US); Siobhan Duffy, Westport (IE); Marine Veronique Germaine Richard, Carrieres sur Seine (FR); Eugene Canavan, Bray (IE); Daniel A. March, Lake Villa, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/529,392

(22) Filed: Dec. 5, 2023

(65) Prior Publication Data
US 2024/0100296 A1 Mar. 28, 2024

Related U.S. Application Data

(60) Continuation of application No. 17/245,280, filed on Apr. 30, 2021, now abandoned, which is a division of
(Continued)

(51) Int. Cl.
*A61M 25/00* (2006.01)

(52) U.S. Cl.
CPC .................. *A61M 25/002* (2013.01)

(58) Field of Classification Search
CPC .................................. A61M 25/002
(Continued)

(56) References Cited

U.S. PATENT DOCUMENTS

D137,496 S 3/1944 Lustig
D139,383 S 11/1944 Lampl
(Continued)

FOREIGN PATENT DOCUMENTS

AT 369994 B 2/1983
CN 2078634 U 6/1991
(Continued)

OTHER PUBLICATIONS

International Search Report and Written Opinion for International Application No. PCT/US2017/028937 dated Aug. 21, 2017.
(Continued)

*Primary Examiner* — Jacob K Ackun
(74) *Attorney, Agent, or Firm* — Cook Alex Ltd.

(57) ABSTRACT

A package for a medical device such as an intermittent catheter has a case and a cap connected by threads. The case includes a hollow tube which is closed at one end and open at the other. A shoulder is formed near one end of the case. Above the shoulder is a cylindrical ferrule that includes external threads. The cap has internal threads selectably engageable with the threads on the ferrule to form a liquid-tight seal between the cap and case when the cap is installed on the case.

20 Claims, 10 Drawing Sheets

Related U.S. Application Data application No. 16/094,912, filed as application No. PCT/US2017/028937 on Apr. 21, 2017, now Pat. No. 11,020,561.

(60) Provisional application No. 62/448,762, filed on Jan. 20, 2017, provisional application No. 62/431,856, filed on Dec. 9, 2016, provisional application No. 62/326,355, filed on Apr. 22, 2016.

(58) Field of Classification Search
USPC .......................................................... 206/364
See application file for complete search history.

(56) References Cited

U.S. PATENT DOCUMENTS

| | | |
|---|---|---|
| 3,114,455 A | 12/1963 | Claisse et al. |
| 3,203,545 A | 8/1965 | Grossman |
| 3,369,542 A | 2/1968 | Thaidigsman |
| 3,794,042 A | 2/1974 | De Klotz et al. |
| 3,854,483 A | 12/1974 | Powers |
| 3,867,945 A | 2/1975 | Long |
| 3,894,540 A | 7/1975 | Bonner, Jr. |
| 3,920,023 A | 11/1975 | Dye |
| 3,934,722 A | 1/1976 | Goldberg |
| 4,043,345 A | 8/1977 | Kramann et al. |
| 4,109,659 A | 8/1978 | Sheridan |
| 4,248,214 A | 2/1981 | Hannah |
| 4,432,758 A | 2/1984 | Finegold |
| 4,553,959 A | 11/1985 | Hickey |
| 4,684,369 A | 8/1987 | Wildemeersch |
| 4,773,901 A | 9/1988 | Norton |
| 4,898,586 A | 2/1990 | McDonough |
| 4,935,017 A | 6/1990 | Sylvanowicz |
| 4,956,298 A | 9/1990 | Diekmann |
| 5,012,940 A | 5/1991 | Koehn |
| 5,084,036 A | 1/1992 | Rosenbaum |
| D327,327 S | 6/1992 | Deguchi et al. |
| 5,149,326 A | 9/1992 | Woodgrift et al. |
| 5,217,114 A | 6/1993 | Gadberry et al. |
| 5,225,165 A | 7/1993 | Perlman |
| 5,380,270 A | 1/1995 | Ahmadzadeh |
| 5,413,561 A | 5/1995 | Fischell et al. |
| 5,417,326 A | 5/1995 | Winer |
| 5,582,599 A | 12/1996 | Daneshvar |
| D381,422 S | 7/1997 | Erskine et al. |
| D383,538 S | 9/1997 | Erskine et al. |
| 5,868,265 A | 2/1999 | Kobayashi |
| 5,881,774 A | 3/1999 | Utterberg |
| 5,919,170 A | 7/1999 | Woessner |
| 6,186,325 B1 | 2/2001 | Schmidt et al. |
| 6,258,078 B1 | 7/2001 | Thilly |
| D449,104 S | 10/2001 | Baker et al. |
| 6,328,355 B1 | 12/2001 | Bortz |
| 6,439,410 B1 | 8/2002 | Dubach |
| 6,460,712 B2 | 10/2002 | Smith et al. |
| 6,460,726 B1 | 10/2002 | Hierzer et al. |
| 6,585,721 B2 | 7/2003 | Fiore |
| 6,634,498 B2 | 10/2003 | Kayerod et al. |
| D488,863 S | 4/2004 | Quinn |
| 6,726,649 B2 | 4/2004 | Swenson et al. |
| 6,822,253 B1 | 11/2004 | Martin et al. |
| 6,871,753 B2 | 3/2005 | McHutchinson |
| 6,908,013 B2 | 6/2005 | Thomson et al. |
| 6,908,113 B2 | 6/2005 | Chaduc |
| 6,926,708 B1 | 8/2005 | Franks-Farah et al. |
| D509,352 S | 9/2005 | Raven et al. |
| 6,964,336 B2 | 11/2005 | Harrold |
| 7,120,487 B2 | 10/2006 | Nelson |
| 7,134,575 B2 | 11/2006 | Vogel et al. |
| 7,306,128 B2 | 12/2007 | Bortz |
| 7,311,698 B2 | 12/2007 | Tanghoj et al. |
| 7,353,969 B2 | 4/2008 | McHutchinson |
| D577,813 S | 9/2008 | Seki et al. |
| D577,814 S | 9/2008 | Seki et al. |
| 7,438,704 B1 | 10/2008 | Kawashima et al. |
| D584,408 S | 1/2009 | Castellani |
| D584,409 S | 1/2009 | Miller et al. |
| D584,410 S | 1/2009 | Miller et al. |
| D588,797 S | 3/2009 | Tanghoej et al. |
| 7,546,931 B2 | 6/2009 | Giusti |
| D595,847 S | 7/2009 | Miller et al. |
| 7,571,804 B2 | 8/2009 | Kjellmann Bruun et al. |
| 7,614,514 B2 | 11/2009 | Fuchs |
| 7,624,868 B2 | 12/2009 | Booker et al. |
| 7,655,063 B2 | 2/2010 | Wang et al. |
| D614,396 S | 4/2010 | Tanghoej et al. |
| 7,699,168 B2 | 4/2010 | Ryan et al. |
| 7,717,284 B2 | 5/2010 | Giusti |
| 7,748,550 B2 | 7/2010 | Cho |
| D630,733 S | 1/2011 | Ahlgren |
| 7,867,220 B2 | 1/2011 | Tanghoj |
| 7,886,907 B2 | 2/2011 | Murray et al. |
| 7,967,744 B2 | 6/2011 | Kaye et al. |
| 7,992,737 B2 | 8/2011 | Salice |
| 8,069,980 B2 | 12/2011 | Stopek et al. |
| 8,137,309 B2 | 3/2012 | Nishtala et al. |
| 8,172,101 B2 | 5/2012 | Giusti |
| 8,181,778 B1* | 5/2012 | van Groningen .. A61M 25/0111 |
| | | 206/364 |
| 8,230,993 B2 | 7/2012 | Tanghoej |
| 8,282,624 B2 | 10/2012 | Tanghoej et al. |
| 8,292,110 B2 | 10/2012 | Rutter et al. |
| D673,264 S | 12/2012 | Kunze |
| 8,361,057 B2 | 1/2013 | Tanghoej et al. |
| 8,381,925 B2 | 2/2013 | Skillin et al. |
| 8,398,615 B2 | 3/2013 | Torstensen et al. |
| 8,434,639 B2 | 5/2013 | Markert |
| 8,439,213 B2 | 5/2013 | Goria et al. |
| 8,448,798 B2 | 5/2013 | Groubert |
| 8,491,568 B2 | 7/2013 | Schertiger et al. |
| 8,511,472 B2 | 8/2013 | Dupuis et al. |
| 8,523,843 B2 | 9/2013 | Kavanagh et al. |
| 8,529,549 B2 | 9/2013 | Tanghoj |
| D691,365 S | 10/2013 | Cote |
| 8,579,115 B2 | 11/2013 | Murphy et al. |
| 8,597,245 B2 | 12/2013 | Jeter et al. |
| 8,616,406 B1 | 12/2013 | Sawicki |
| 8,616,407 B2 | 12/2013 | Sawicki |
| D705,925 S | 5/2014 | Murray et al. |
| 8,721,676 B1 | 5/2014 | Janardhan et al. |
| 8,733,566 B2 | 5/2014 | Druitt et al. |
| D707,351 S | 6/2014 | Kunze |
| 8,752,722 B2 | 6/2014 | Kuhn et al. |
| 8,863,968 B2 | 10/2014 | Giusti |
| D724,199 S | 3/2015 | Bambot et al. |
| 9,033,149 B2* | 5/2015 | Terry ..................... A61F 2/042 |
| | | 604/172 |
| 9,090,386 B2 | 7/2015 | van Alfen et al. |
| D738,973 S | 9/2015 | Dingman |
| D739,932 S | 9/2015 | Ratjen et al. |
| 9,220,866 B2 | 12/2015 | Van Groningen et al. |
| D747,184 S | 1/2016 | Murray et al. |
| 9,277,966 B2 | 3/2016 | Seitz, III |
| 9,334,097 B2 | 5/2016 | Skillin et al. |
| 9,352,318 B2 | 5/2016 | Giusti |
| D760,490 S | 7/2016 | Johnson |
| 9,415,909 B2 | 8/2016 | Druitt et al. |
| 9,422,089 B2 | 8/2016 | Wheeler |
| 9,501,958 B2 | 11/2016 | Pietarinen et al. |
| 9,511,906 B2 | 12/2016 | van Alfen et al. |
| 9,669,187 B2 | 6/2017 | Tjassens et al. |
| 9,687,629 B1 | 6/2017 | Palmer |
| 9,701,451 B2 | 7/2017 | Skillin et al. |
| D796,025 S | 8/2017 | Lo |
| 10,561,817 B2 | 2/2020 | Hannon et al. |
| 10,857,068 B2 | 12/2020 | Davis et al. |
| 10,912,918 B1* | 2/2021 | Palmer ............... A61M 27/00 |
| 11,020,561 B2* | 6/2021 | O'Brien ............. A61M 25/002 |
| 2001/0001443 A1* | 5/2001 | Kayerod ............. A61M 25/002 |
| | | 206/364 |
| 2001/0037954 A1* | 11/2001 | Schmidt .............. A61M 25/002 |
| | | 206/439 |
| 2003/0004496 A1 | 1/2003 | Tanghoj |

(56) References Cited

U.S. PATENT DOCUMENTS

| | | |
|---|---|---|
| 2003/0060807 A1 | 3/2003 | Tanghoj |
| 2003/0141210 A1* | 7/2003 | Yanke ............... B65D 25/14 |
| | | 206/524.4 |
| 2004/0016714 A1 | 1/2004 | Wood |
| 2004/0150221 A1 | 8/2004 | Brown |
| 2004/0158231 A1 | 8/2004 | Tanghoj et al. |
| 2005/0043715 A1 | 2/2005 | Nestenberg |
| 2005/0067366 A1 | 3/2005 | Dubach |
| 2005/0106339 A1 | 5/2005 | Baker |
| 2005/0106340 A1 | 5/2005 | Baker |
| 2005/0274687 A1 | 12/2005 | McCutchan |
| 2006/0091670 A1 | 5/2006 | Gaynor |
| 2006/0116661 A1 | 6/2006 | Tanghoj |
| 2006/0142737 A1 | 6/2006 | Tanghoj |
| 2006/0180585 A1 | 8/2006 | Cunningham et al. |
| 2007/0034537 A1* | 2/2007 | Fago ............... G21F 5/018 |
| | | 250/506.1 |
| 2007/0068977 A1 | 3/2007 | Vogel et al. |
| 2008/0033371 A1 | 2/2008 | Updegraff et al. |
| 2008/0183181 A1 | 7/2008 | Treacy et al. |
| 2008/0264961 A1 | 10/2008 | Sawyer |
| 2008/0289984 A1 | 11/2008 | Raven |
| 2008/0319423 A1* | 12/2008 | Tanghoj ............ B65D 77/20 |
| | | 206/364 |
| 2009/0008279 A1* | 1/2009 | Tanghoej ......... A61M 25/002 |
| | | 206/364 |
| 2009/0050253 A1 | 2/2009 | Thomas et al. |
| 2009/0054876 A1 | 2/2009 | Borodulin |
| 2009/0131917 A1 | 5/2009 | Kavanagh et al. |
| 2009/0166361 A1 | 7/2009 | Lourenco |
| 2009/0299334 A1* | 12/2009 | Nishtala ......... A61M 25/002 |
| | | 604/533 |
| 2010/0087801 A1* | 4/2010 | Torstensen ...... A61M 25/002 |
| | | 206/364 |
| 2010/0106236 A1 | 4/2010 | Nelson |
| 2010/0211050 A1 | 8/2010 | Luther |
| 2010/0224643 A1 | 9/2010 | Daggett |
| 2010/0252469 A1 | 10/2010 | Tanghoej |
| 2010/0256580 A1 | 10/2010 | Faber |
| 2010/0324540 A1 | 12/2010 | Paulen et al. |
| 2011/0060317 A1 | 3/2011 | Frojd |
| 2011/0224653 A1 | 9/2011 | Torstensen |
| 2012/0016318 A1 | 1/2012 | Hoang et al. |
| 2012/0051967 A1* | 3/2012 | Murphy ............ A61M 5/002 |
| | | 206/365 |
| 2012/0165791 A1 | 6/2012 | Lovmar |
| 2012/0168324 A1 | 7/2012 | Carleo |
| 2012/0179144 A1 | 7/2012 | Carleo |
| 2012/0271281 A1 | 10/2012 | Schertiger |
| 2013/0068767 A1 | 3/2013 | Fraser et al. |
| 2013/0134123 A1 | 5/2013 | Fraser |
| 2013/0150828 A1 | 6/2013 | Conway |
| 2013/0161344 A1 | 6/2013 | Park et al. |
| 2013/0186791 A1 | 7/2013 | Triquigneaux |
| 2013/0218136 A1 | 8/2013 | Tanghoej et al. |
| 2013/0240393 A1* | 9/2013 | Bode ............... A61M 5/002 |
| | | 206/363 |
| 2013/0261608 A1 | 10/2013 | Tanghoj |
| 2013/0289537 A1 | 10/2013 | Schertiger |
| 2013/0292286 A1 | 11/2013 | Van Groningen |
| 2013/0299516 A1 | 11/2013 | Dupuis et al. |
| 2013/0327664 A1 | 12/2013 | Tanghoj |
| 2014/0262860 A1 | 9/2014 | Hagel |
| 2014/0262903 A1 | 9/2014 | Mitten et al. |
| 2014/0263436 A1 | 9/2014 | Gelov et al. |
| 2014/0360896 A1 | 12/2014 | Torstensen |
| 2015/0018803 A1 | 1/2015 | Tjassens et al. |
| 2015/0352321 A1 | 12/2015 | Hannon et al. |
| 2016/0016703 A1 | 1/2016 | Mühlemann |
| 2016/0023818 A1 | 1/2016 | Gelov et al. |
| 2016/0038717 A1 | 2/2016 | Murray et al. |
| 2016/0059999 A1 | 3/2016 | Fraser et al. |
| 2016/0172742 A1 | 6/2016 | Forster |
| 2016/0193447 A1 | 7/2016 | Matthiassen |
| 2016/0228872 A1 | 8/2016 | Giusti |
| 2016/0325895 A1 | 11/2016 | Browning, Jr. |
| 2016/0332789 A1 | 11/2016 | Yerecic |
| 2017/0014597 A1 | 1/2017 | Hagel |
| 2017/0080177 A1 | 3/2017 | Tanghoej et al. |
| 2017/0107365 A1 | 4/2017 | Rycroft et al. |
| 2017/0166369 A1 | 6/2017 | Mitten et al. |
| 2017/0173300 A1 | 6/2017 | Hannon et al. |
| 2017/0175428 A1 | 6/2017 | Quinn et al. |
| 2017/0326334 A1 | 11/2017 | Terry |

FOREIGN PATENT DOCUMENTS

| | | |
|---|---|---|
| CN | 2340720 | 9/1999 |
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 102004013712 B3 | 8/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 202011107025 | 3/2013 |
| DE | 202011107059 | 3/2013 |
| DE | 102013014483 A1 | 6/2014 |
| DE | 202017101126 U | 4/2017 |
| DE | 102016205834 B3 | 5/2017 |
| DK | 173714 B1 | 7/2001 |
| EP | 0781572 A2 | 7/1977 |
| EP | 0041487 A | 12/1981 |
| EP | 0134630 A | 3/1985 |
| EP | 0861639 A2 | 9/1998 |
| EP | 0910425 A1 | 4/1999 |
| EP | 0923398 A1 | 6/1999 |
| EP | 0812287 B1 | 11/1999 |
| EP | 0996542 A1 | 5/2000 |
| EP | 1023882 A1 | 8/2000 |
| EP | 0933304 B1 | 3/2003 |
| EP | 1086024 B1 | 5/2003 |
| EP | 1963195 A2 | 5/2003 |
| EP | 1334039 A1 | 8/2003 |
| EP | 1466645 A2 | 10/2004 |
| EP | 1392575 B1 | 9/2005 |
| EP | 1593710 A1 | 11/2005 |
| EP | 1607344 | 12/2005 |
| EP | 1615960 A1 | 1/2006 |
| EP | 1317382 B1 | 3/2006 |
| EP | 1634554 A2 | 3/2006 |
| EP | 1638856 A1 | 3/2006 |
| EP | 1671663 A1 | 6/2006 |
| EP | 1696990 A1 | 9/2006 |
| EP | 1487712 B1 | 10/2006 |
| EP | 1278679 B1 | 6/2007 |
| EP | 1858575 | 11/2007 |
| EP | 1863719 A2 | 12/2007 |
| EP | 1799574 B1 | 1/2008 |
| EP | 1878461 A1 | 1/2008 |
| EP | 1897579 A1 | 3/2008 |
| EP | 1897580 A1 | 3/2008 |
| EP | 1409369 B1 | 7/2008 |
| EP | 1979032 A1 | 10/2008 |
| EP | 1982741 A2 | 10/2008 |
| EP | 1720772 A1 | 11/2008 |
| EP | 1986921 A1 | 11/2008 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2295108 | 3/2011 |
| EP | 22922294 A1 | 3/2011 |
| EP | 2308543 A1 | 4/2011 |
| EP | 1966058 B1 | 7/2011 |
| EP | 2450076 A1 | 5/2012 |
| EP | 2468319 A1 | 6/2012 |
| EP | 2325100 B1 | 8/2012 |

(56) References Cited

FOREIGN PATENT DOCUMENTS

| | | |
|---|---|---|
| EP | 2504054 A1 | 10/2012 |
| EP | 2515985 A1 | 10/2012 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2682069 A1 | 1/2014 |
| EP | 2686054 A1 | 1/2014 |
| EP | 2750748 A1 | 7/2014 |
| EP | 2250102 B1 | 9/2014 |
| EP | 2774648 A1 | 9/2014 |
| EP | 2785409 A1 | 10/2014 |
| EP | 2823845 A1 | 1/2015 |
| EP | 2782842 B1 | 7/2015 |
| EP | 3033279 A1 | 6/2016 |
| EP | 3038075 A2 | 6/2016 |
| EP | 2576374 B1 | 9/2016 |
| EP | 3113922 A1 | 1/2017 |
| EP | 2605977 B1 | 5/2017 |
| EP | 3210909 A1 | 8/2017 |
| EP | 3248620 A1 | 11/2017 |
| FR | 2717676 A1 | 9/1995 |
| FR | 2801567 | 6/2001 |
| GB | 2031735 A | 4/1980 |
| GB | 2033231 A | 5/1980 |
| GB | 2322079 A | 8/1998 |
| JP | 2001025473 | 1/2001 |
| KR | 20110101674 | 7/2012 |
| PT | 2216064 T | 9/2016 |
| SE | 514121 C2 | 1/2001 |
| WO | WO 9608219 A1 | 3/1996 |
| WO | WO 9726937 A1 | 7/1997 |
| WO | WO 9741811 A1 | 11/1997 |
| WO | WO 9811932 A1 | 3/1998 |
| WO | WO 9819729 A1 | 5/1998 |
| WO | WO 9930761 A1 | 6/1999 |
| WO | WO 9942155 A2 | 8/1999 |
| WO | WO 0016843 A1 | 3/2000 |
| WO | WO 0030575 A1 | 6/2000 |
| WO | WO 0047494 A1 | 8/2000 |
| WO | WO 0143807 A1 | 6/2001 |
| WO | WO 0160255 A1 | 8/2001 |
| WO | WO 02060361 A2 | 8/2002 |
| WO | WO 02080843 A2 | 10/2002 |
| WO | WO 03001994 A1 | 1/2003 |
| WO | WO 03008028 A2 | 1/2003 |
| WO | WO 03008029 A2 | 1/2003 |
| WO | WO 03022561 A1 | 3/2003 |
| WO | WO 03045487 A2 | 6/2003 |
| WO | WO 03061732 A2 | 7/2003 |
| WO | WO 03092779 A1 | 11/2003 |
| WO | WO 03097237 A2 | 11/2003 |
| WO | WO 2004/021890 A1 | 3/2004 |
| WO | WO 2004/032750 A1 | 4/2004 |
| WO | WO 2004/035123 A1 | 4/2004 |
| WO | WO 2004/050155 A1 | 6/2004 |
| WO | WO 2004/054446 A1 | 7/2004 |
| WO | WO 2004/054653 | 7/2004 |
| WO | WO 2004/056414 | 7/2004 |
| WO | WO 2004/089454 A1 | 10/2004 |
| WO | WO 2004/103153 A2 | 12/2004 |
| WO | WO 2005/014055 A2 | 2/2005 |
| WO | WO 2005/056414 | 6/2005 |
| WO | WO 2005/092418 A1 | 10/2005 |
| WO | WO 2006/005349 A2 | 1/2006 |
| WO | WO 2006/017439 A2 | 2/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/092150 A1 | 9/2006 |
| WO | WO 2006/121183 A1 | 11/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009/017541 A1 | 2/2009 |
| WO | WO 2009/068043 A2 | 6/2009 |
| WO | WO 2009/139878 A1 | 11/2009 |
| WO | WO 2010/006620 A1 | 1/2010 |
| WO | WO 2010/130261 A1 | 11/2010 |
| WO | WO 2011/011023 | 1/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011/079129 A1 | 6/2011 |
| WO | WO 2011/109393 A1 | 9/2011 |
| WO | WO 2011/147803 A1 | 12/2011 |
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/060699 A1 | 5/2012 |
| WO | WO 2012/079590 A1 | 6/2012 |
| WO | WO 2012/085107 A2 | 6/2012 |
| WO | WO 2012/110755 A1 | 8/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012/166045 A1 | 12/2012 |
| WO | WO 2012/166967 A1 | 12/2012 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013/083137 A1 | 6/2013 |
| WO | WO 2013/098190 A1 | 7/2013 |
| WO | WO 2013/105091 A1 | 7/2013 |
| WO | WO 2014/062223 A1 | 4/2014 |
| WO | WO 2014/062225 A1 | 4/2014 |
| WO | WO 2014/063711 A1 | 5/2014 |
| WO | WO 2014/074141 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/065725 A1 | 5/2015 |
| WO | WO 2015/066673 A1 | 5/2015 |
| WO | WO 2015/075841 A1 | 5/2015 |
| WO | WO 2015120119 A1 | 8/2015 |
| WO | WO 2015/184365 | 12/2015 |
| WO | WO 2016/044379 A2 | 3/2016 |
| WO | WO 2016/094606 A1 | 6/2016 |
| WO | WO 2017/024106 A1 | 2/2017 |
| WO | WO 2017/174715 | 10/2017 |
| WO | WO 2017/185029 A1 | 10/2017 |
| WO | WO 2017/185052 A1 | 10/2017 |

(56) References Cited

FOREIGN PATENT DOCUMENTS

OTHER PUBLICATIONS

International Search Report dated Feb. 24, 2015, for International Application No. PCT/US2014/053573.
International Search Report and Written Opinion for International Application No. PCT/US2015/033344 dated Mar. 12, 2015.
Total Body Relief and Hygiene for Travel, Home bath, and life's less comfortable moments, http://www.biorelief.com/blog/self-cath-fits-in-your-pocket/ dated Apr. 19, 2014.

* cited by examiner

MEDICAL DEVICE PACKAGE WITH A TWIST CAP

CROSS-REFERENCE TO RELATED APPLICATIONS

The present application is a continuation of U.S. patent application Ser. No. 17/245,280, filed Apr. 30, 2021, which is a divisional of U.S. patent application Ser. No. 16/094,912, filed Oct. 19, 2018, which is a National Stage Application of PCT International Application No. PCT/US2017/028937, filed Apr. 21, 2017 which claims the benefit of and priority to: U.S. Provisional Patent Application No. 62/326,355, filed Apr. 22, 2016; U.S. Provisional Patent Application No. 62/431,856, filed Dec. 9, 2016; and U.S. Provisional Patent Application No. 62/448,762, filed Jan. 20, 2017; the disclosures of all of which are hereby incorporated herein by reference.

FIELD OF THE DISCLOSURE

This disclosure relates generally to packaging for medical devices such as urinary catheters. More particularly, this disclosure relates to compact catheters, such as urinary catheters, and the packaging, storing and hydrating/lubricating of such catheters.

BACKGROUND

Intermittent catheterization is a good option for many users who suffer from various abnormalities of the urinary system. Very often, such abnormalities of the urinary system are caused by a spinal cord injury which may also result in diminished dexterity of the user.

Commonly, in intermittent catheterization, a single use, individually packaged, sterile catheters are used. Catheters often include a surface treatment that reduces friction to allow for easier and less traumatic insertion into and through the user's urethra.

Regardless of whether a surface treatment is used or what type of surface treatment is used, some type of package for the catheter is required. In the past various kinds of packages have been used, including molded containers of assorted sizes and shapes, bags and pouches made of plastic or metal foil, and similar kinds of devices While these prior art packages generally accomplish the objective of protecting the catheter during transport, storage and preparation for use, they suffer from disadvantages that range from fundamental—the packages break open prematurely; to economic—the package designs are wasteful of material and labor; to the annoying—the packages confuse users as to how to open them, or the packages tend to spill the hydrating medium upon opening. What is needed is a catheter package that is economical to manufacture and fill, reliable throughout its useful life, and simple and intuitive to use. It is also desirable to have a compact package which is: discreet to carry before use; discrete to dispose of in a waste bin; and intuitive and easy to open. Additional desirable features of the package include easy removal of the catheter from the case; easy reclosing of the case after use; hygienic use; and it should be discreet and clean to carry after use.

SUMMARY

In one aspect, the present disclosure includes a hard plastic packaging that holds a short, hydrophilic coated catheter. The catheter may have a length of, by way of example only, about 91 mm of exposed length. A funnel is attached to the catheter. The funnel may be, for example, about 40 mm long. The hard packaging includes a case that enables the properties of vapor hydration through a hydration liner that separates a water chamber from the hydrophilic coated catheter. A twist cap is provided that attaches to the case to form a hygienic seal.

In one embodiment of the present disclosure, the package case has a hollow plastic tube for receiving the catheter. The tube has a wall closed at one end by a bottom wall. Toward the opposite end of the wall there is a radially extending shoulder. Above the shoulder there is a cylindrical ferrule which is open at its end and defines a rim. External threads are formed on the outer surface of the ferrule. A cap may be removably attached to the ferrule by threads. The cap is selectably installed or removed from the case such that the cap covers or uncovers the open end of the ferrule, respectively. The cap may have a skirt which carries internal threads that engages with the mating threads on the ferrule.

The internal wall of the cap has a seal bead extending radially inwardly just above the threads. The seal bead is engageable with the external wall of the ferrule. Alternatively, the external wall of the ferrule could have a seal bead extending radially outwardly just above the threads that is engageable with the internal wall of the cap. The seal beads are located above the threads instead of below them. This provides a manufacturing advantage in that the parts can be made narrower. Furthermore, there is no seal between the bottom of the cap and the shoulder on the case. That area is vented so an interior seal can be tested in a vacuum test.

The product is opened by twisting the cap one quarter turn. The opening torque is selected to be small enough to make the cap easy to open but great enough such that the cap will not release by itself or under normal handling conditions. Once the cap is off the case, it exposes the catheter which can then be picked up by the user. Once the cap is twisted open, the sterile seal that existed between the case and cap is breached and the catheter is no longer contained in a sterile environment and is ready to use. During use of the catheter the cap may be temporarily stored on the bottom of the case where the cap may be attached by a snap fit. When the cap is removed and the catheter removed, the user can re-capture the catheter in the case for disposal if they so wish. Once the cap is back into its original state the packaging retains its original sealing qualities (meaning it will not leak), with the tamper evident feature the only indicator that the product has been used.

DETAILED DESCRIPTION OF THE EMBODIMENTS

Figures 1, 2:
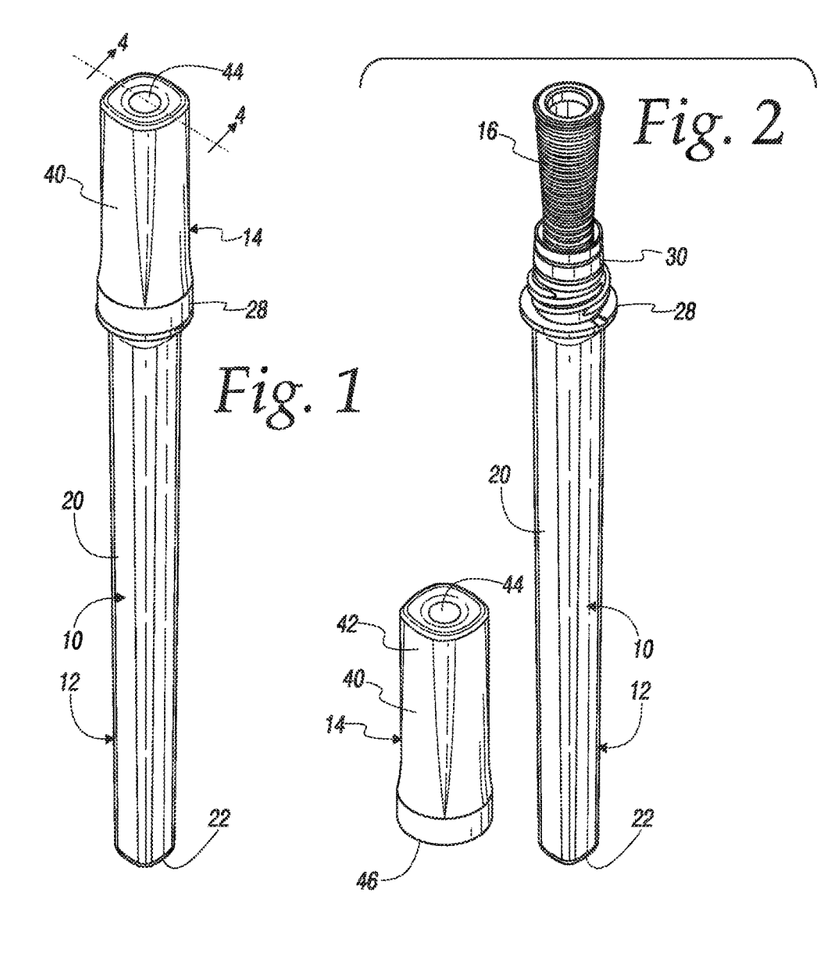
FIG. 1 is a perspective view of the catheter package of the disclosure, showing the cap installed on the case in a closed condition.
FIG. 2 is a perspective view of the catheter package of the disclosure, showing the cap removed from the case to expose a funnel portion of a catheter in the case.
Figure 3:
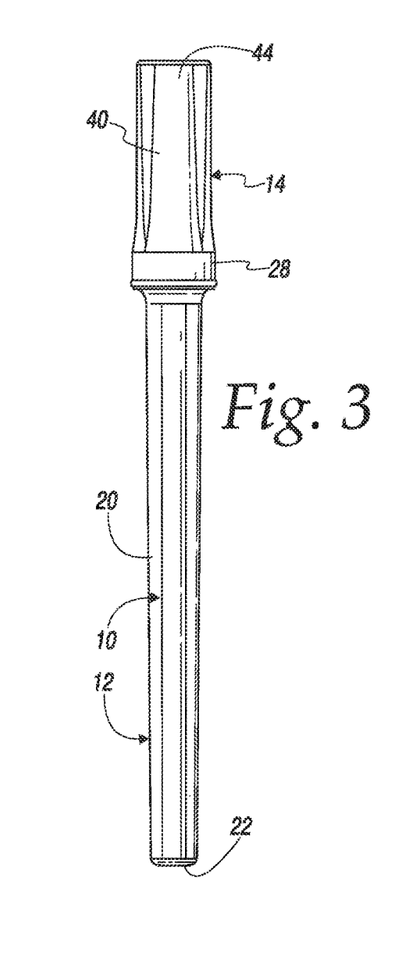
FIG. 3 is a side elevation view of the package of FIG. 1.

The present disclosure is directed to packages for medical devices such as intermittent urinary catheters. The package is shown generally at 10 in FIGS. 1-3. The major components of the package are a case 12 and a cap 14. The cap is threadably engageable with the case such that a user can selectably remove the cap from the case and subsequently replace the cap on the case. FIGS. 1 and 3 show the cap installed on the case so the package is in a closed condition. FIG. 2 shows the cap removed from the case and resting adjacent the case so the package is in an open condition. With the case open the funnel 16 of a catheter is visible protruding above the case. The tube portion of the catheter is within the case and thus not shown in FIGS. 1-3 but the catheter tube 18 is visible in FIGS. 4-6.

Figure 3A:
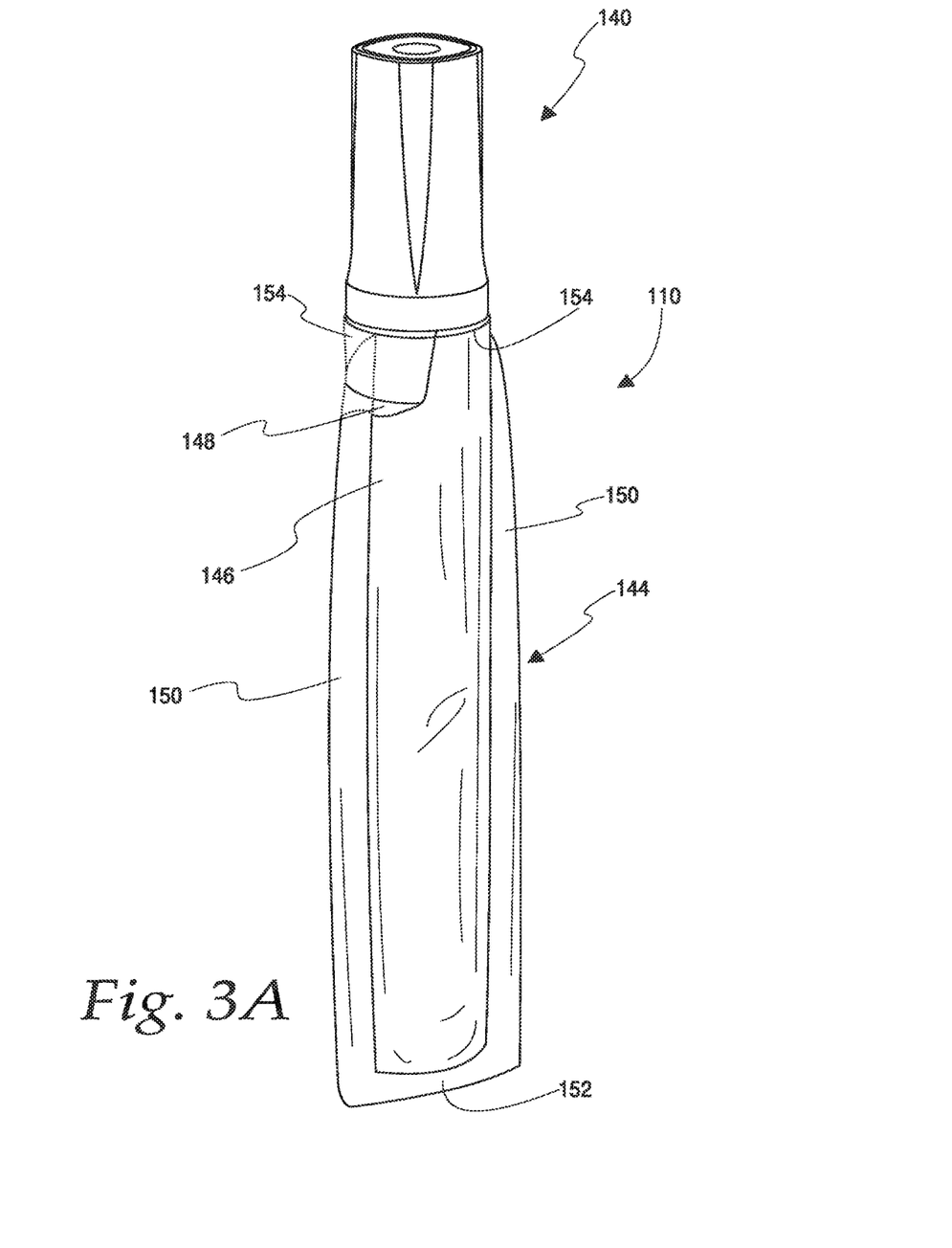
FIG. 3A is a perspective view of another embodiment of a package assembly of the present disclosure.

FIG. 3A illustrates another embodiment of the present disclosure wherein the top 140 of the package 110 has any of features disclosed herein but the bottom 144 of the package 142, which forms or defines the hollow tube that houses the catheter tube, is made from a flexible material. For example, the bottom 144 of the package 110 may be made from one or more flexible polymeric and/or metal foil sheets. The sheet may be a laminate that includes both polymeric and metal layers. In the illustrated embodiment, the bottom 144 of the package 110 may be formed from a front sheet 146 and a back sheet 148 wherein the sheets 146 and 148 are sealed together along the side edges 150 and bottom edge 152. The top edges 154 of the sheets 146 and 148 may be attached to the top 140 of the package 142, by for example, adhesive or welding.

Details of the case 12 will now be described in connection with FIGS. 4-6. The case includes a hollow tube 20 which terminates at an end wall 22 that closes the bottom of the tube 20. The tube 20 is shown here with a generally rectangular cross-sectional shape. It will be understood the cross-sectional shape could alternately be cylindrical or otherwise. As can be best seen in FIG. 6 the upper end of the tube 20 has an internal rib 24 that protrudes radially inwardly from the internal wall surface of the tube 20. Just above the rib 24 is a radially inwardly protruding lip 26. The rib 24 and lip 26 cooperate to locate and support a hydration liner that will be described below in connection with FIGS. 7-10.

The rib 24 and lip 26 are axially located in an area of the tube 20 where the external wall of the tube has a radially outwardly extending shoulder 28. Above the shoulder 28 there is a cylindrical ferrule 30. The ferrule terminates at an open end which defines a rim 32. In some respects the ferrule 30 can be considered part of the upper end of the tube 20. External threads 34 are formed on the external surface of the ferrule 30. Above the threads 34 is an external bead 36. A similar internal bead 38 is formed on the internal wall of the ferrule. Internal bead is axially located about even with the bottom thread 34. The internal bead 38 may engage the bottom edge of the catheter funnel 16, as best seen in FIGS. 5 and 6, to lightly secure the catheter in the case. This retaining feature will prevent inadvertent removal of the catheter should an open case be turned upside down.

Details of the cap 14 will now be described in connection with FIGS. 4-6. The cap includes a hollow shell 40 which has a longitudinal wall 42 and terminates at a top wall 44 that closes the top of the shell 40. The longitudinal wall 42 of the shell 40 is shown here with a generally rectangular cross-sectional shape. It will be understood the cross-sectional shape could alternately be cylindrical or otherwise. The longitudinal wall 42 tapers radially outwardly toward its open bottom end 46. This tapered portion defines a skirt 48. On the interior wall of the shell, axially located about where the skirt 48 begins, there is an internal bead 50. This internal bead 50 cooperates with the external bead 36 on the ferrule 30 to form a liquid-tight seal between an installed cap 14 and the case 12. This axial location of the cooperating beads 36 and 50 affords a more compact construction of the parts than would be the case if the beads were axially located near the open bottom end 46 of the shell 40.

The skirt 48 of the cap also has on its internal wall three threads 52. These threads are engageable with the threads 34 on the ferrule. As best seen in FIG. 2, the threads 52 are not continuous with one another. Instead, they are separate from one another and extend circumferentially approximately 90°. With this design a quarter turn of the cap will release or engage the threads.

Figures 4, 5, 6:
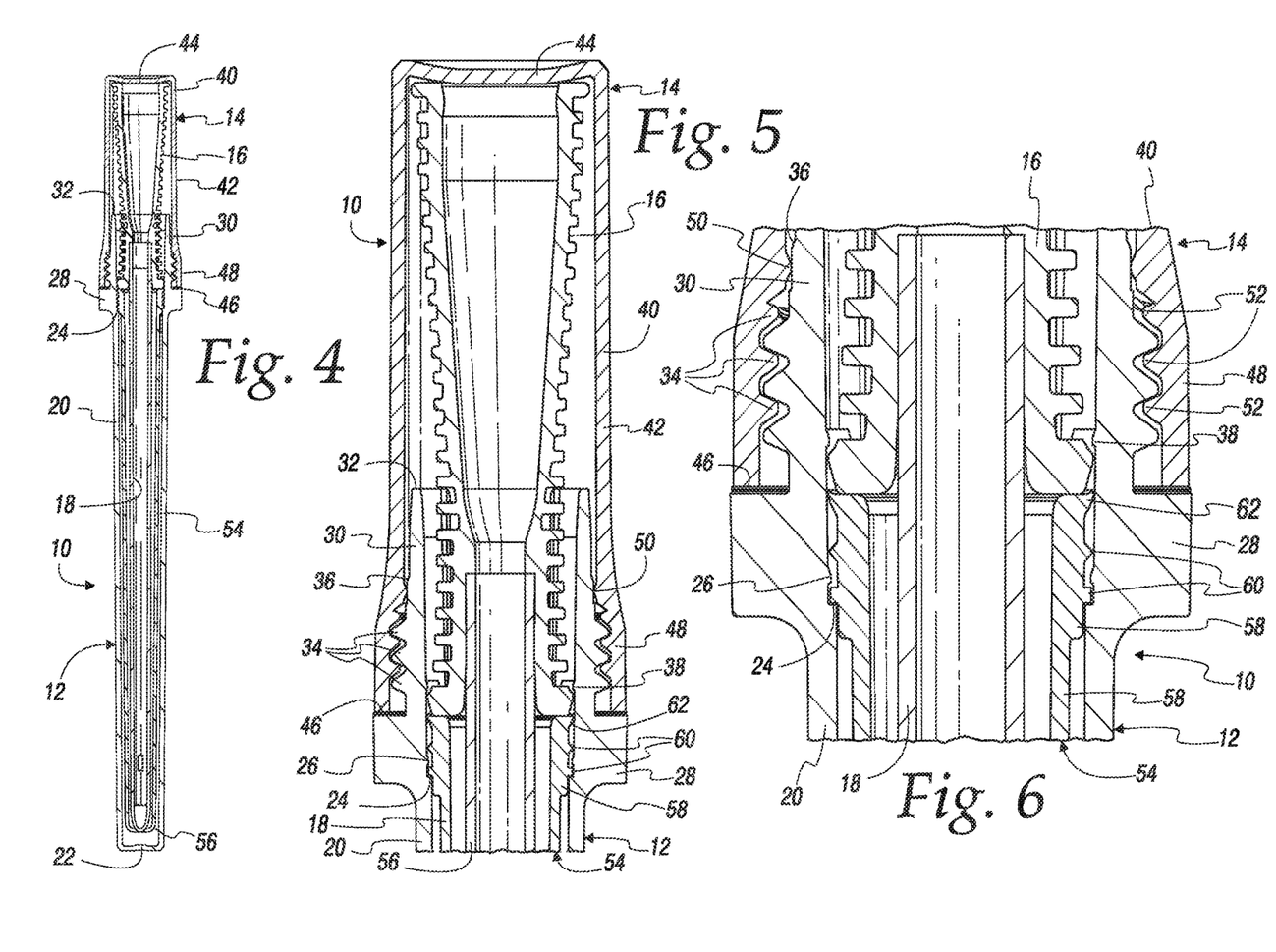
FIG. 4 is a vertical section taken along line 4-4 of FIG. 1.
FIG. 5 is a section similar to FIG. 4 showing the cap and upper end of the case on an enlarged scale.
FIG. 6 is a section similar to FIG. 5 showing the engaging threads of the cap and ferrule on a further enlarged scale.

As shown in FIGS. 5 and 6 and explained above, upon opening of the package 10, the distal end of the funnel 16 projects above the rim 32 and extends or projects out of the opening of the package so that the funnel 16 may be accessed and grasped by the user to remove the catheter 18 from the package. As also discussed above, the catheter 18 is retained within the package by, for example, an interaction between the internal bead or rib 38 of case 12 and flange of the funnel 16, until the user applies sufficient force to remove the catheter from the package. For example, axial movement of the catheter to move the flange past the rib 38. One of the benefits of this retention feature is that the engagement between the catheter 18 and the case 12 resists inadvertent removal of the catheter 18 so that the catheter 18 remains within the opened package 10 until the user actively removes the catheter 18 for use. In other words, the retention feature prevents the catheter 18 from inadvertently falling out of the package 10. For in conventional package assemblies wherein the catheter may inadvertently fall out of the package, the catheter is at risk of coming into contact with surfaces that may contaminate the catheter which can result in increasing the risk of infection. Thus, retaining the catheter 18 within the opened package 10 until it is ready for use can assist in reducing the risk of undesired contamination. This is particularly useful for individuals with limited dexterity and for those who have the habit of commencing the catheterization procedure by opening the package and then proceeding with the other steps of the catheterization procedure.

Referring to FIGS. 6A-6D, there are some catheterization procedures that require the use of a urine collection bag 130 and/or the user prefers to use a urine collection bag 130. In catheterization procedures that use a urine collection bag 130, each of the features of the catheter extending beyond rim 32 the opening of the package 10 and the catheter retention feature may provide benefits to the user.

Figures 6A, 6B:
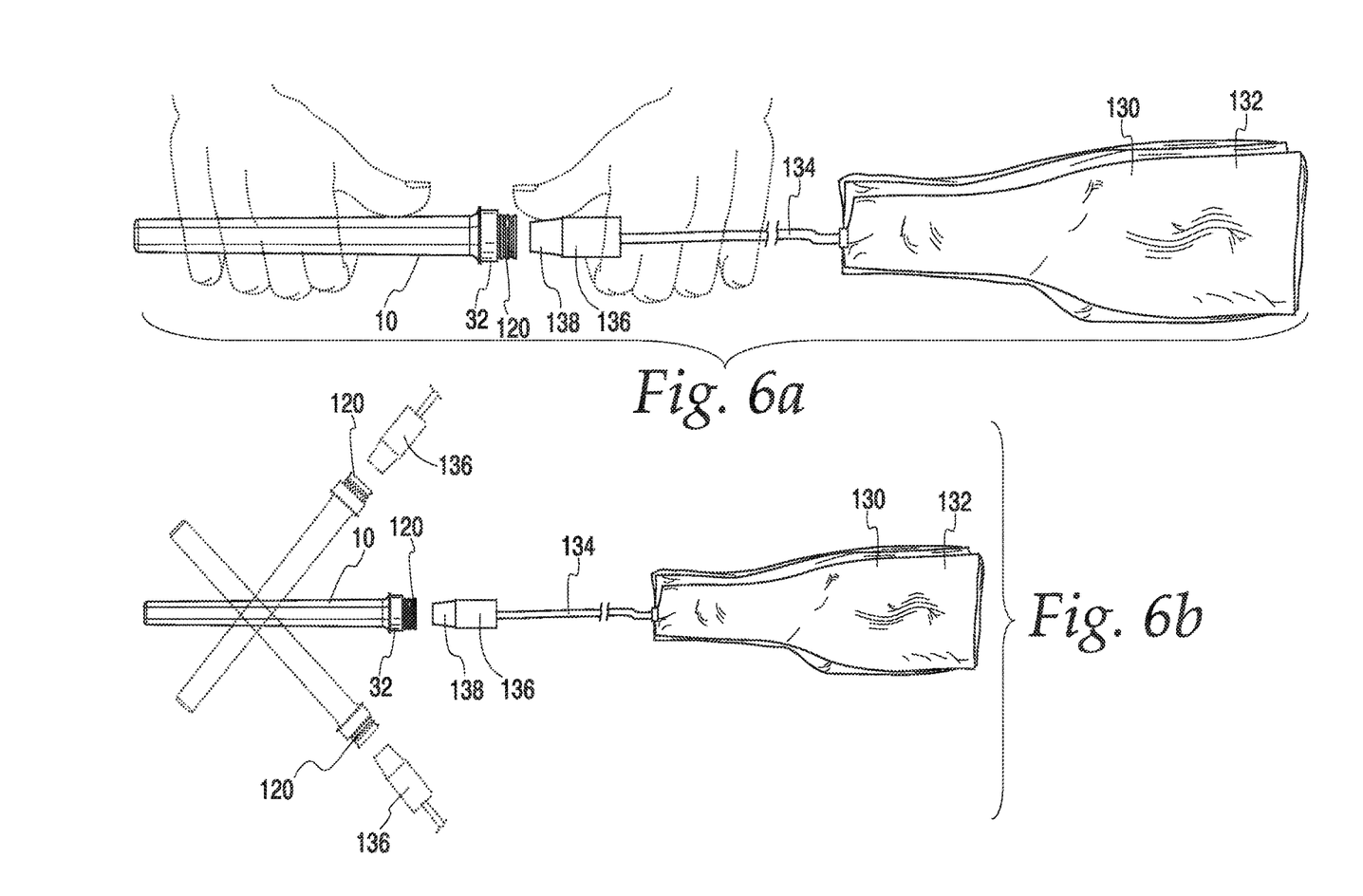
FIG. 6A is a perspective view showing a user connecting a urine collection bag to the catheter assembly.
FIG. 6B is a perspective view illustrating that the package assembly may be positioned in different orientations during connection to the urine collection bag.
Figure 6C:
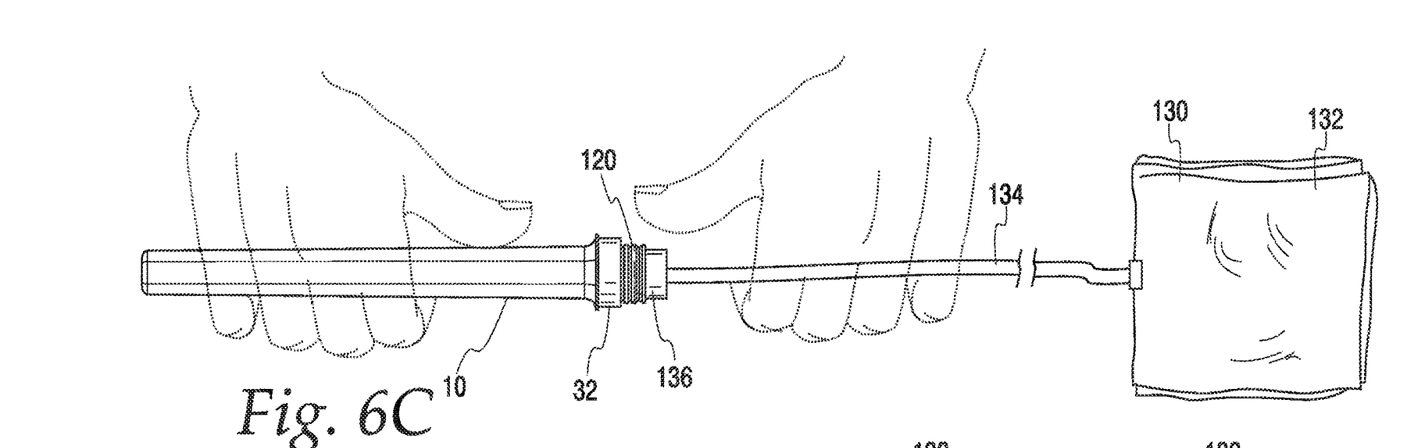
FIG. 6C is a perspective view showing the urine collection bag attached to the funnel of the catheter.
Figure 6D:
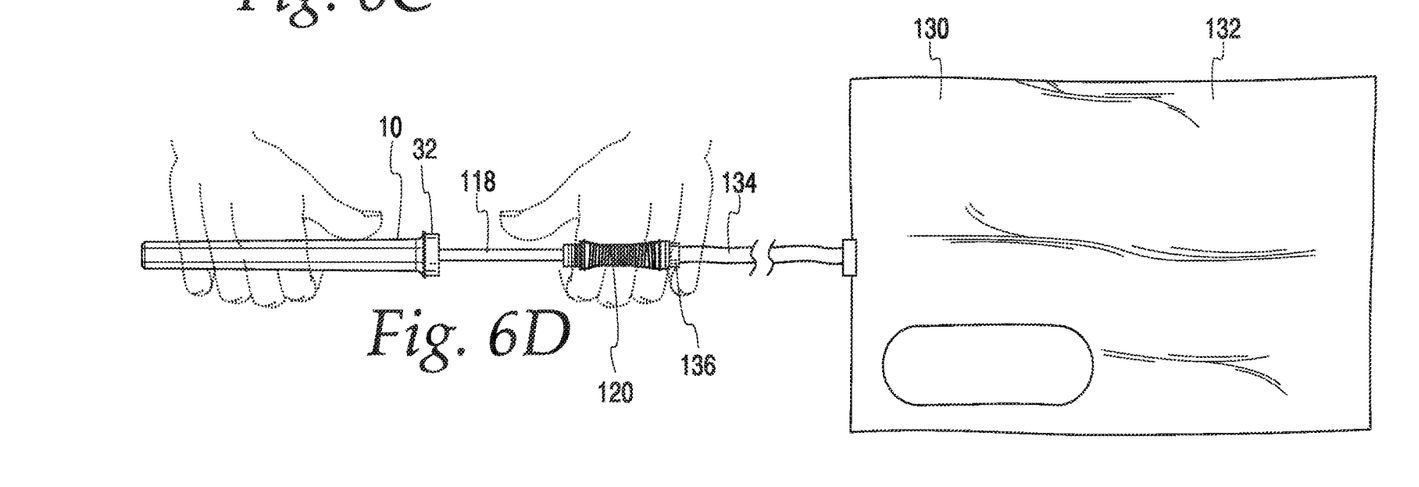
FIG. 6D is a perspective view of the catheter being removed from the package assembly.
Figures 7, 8, 9, 10:
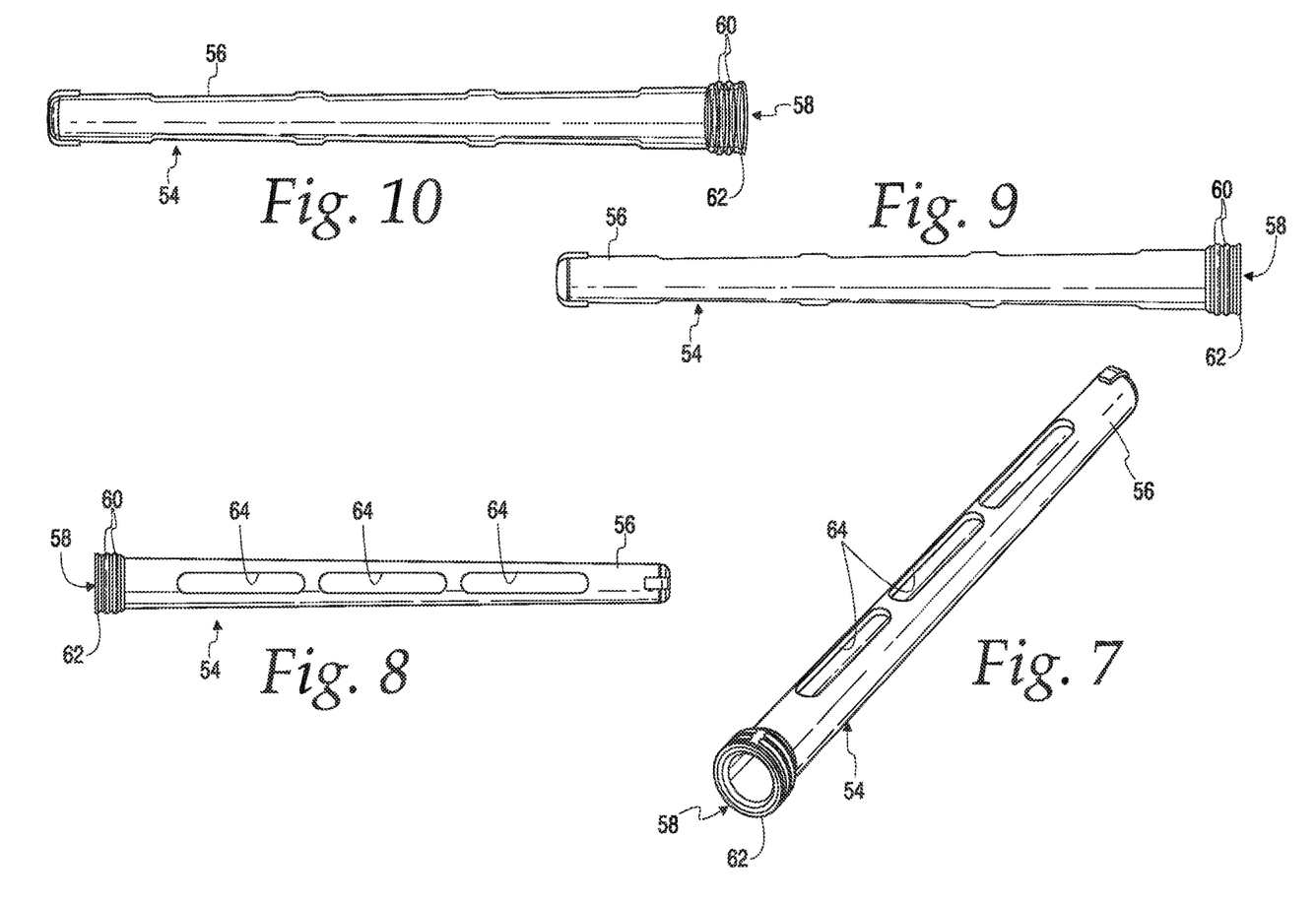
FIG. 7 is a perspective view of a hydration liner that can be used in the package of the present disclosure.
FIG. 8 is a top plan view of the hydration liner of FIG. 7.
FIG. 9 is a side elevation view of the hydration liner.
FIG. 10 is a longitudinal section through the hydration liner.

Turning first to the retaining feature, which retains the catheter 118 within the package 10 until the user applies sufficient force to the catheter 118 to remove it from the package 10. Referring to FIG. 6A, for illustrative purposes, there is shown a typical urine collection bag 130 that includes a urine collection reservoir 132, such as a plastic bag, a tube 134 for the passage of urine into the collection reservoir 132 and a connector 136 that connects the tube 134 to the funnel 120 of the catheter. In the illustrated embodiment, the connector 136 may include a tapered end portion 138 which is sized to be fitted within the opening of the funnel 120 and be retained within the funnel 120 by a friction fit. Referring to FIGS. 6A and 6B, to connect the urine collection bag 130 to the funnel 120, the connector 136 is inserted into the funnel 120 and force is applied to securely fit the connector within the funnel.

In conventional packages already know in the field, the user first removes the catheter from the package and then attaches the urine collection bag to the funnel by grasping the funnel. While connecting the collection bag to the funnel, the user tries to avoid contact with the catheter tube, so as to avoid contamination thereof. This may be difficult for users with limited dexterity and may lead to an increased risk of contamination.

Turning back to FIGS. 6A-6D, because the catheter 118 is securely retained within the package 10 and the user does not have to be concerned with the catheter 118 inadvertently falling out of the package, the user may grasp the outside of the package 10 (as opposed to only grasping the funnel) to connect the urine collection bag 130 without having to first remove the catheter from the package. The ability to be able to grip the outside of the package 10 provides a larger gripping surface for the user for the user to manipulate the catheter 118 and also reduces the risk of contamination because the catheter 118 remains protected within the package 10 during connection of the connector 136 and the funnel 120. Furthermore, as shown in FIG. 6B, after opening of the catheter package 10, the package 10 may be held in virtually any orientation without the concern of the catheter 118 falling out of the package 10. This can be beneficial to users with limited dexterity, especially those that would need to hold the package 10 upside down or with the opening in a downward orientation in order to connect the urine collection bag 130 to the catheter funnel 120.

Regarding the distal end of the funnel 120 extending above the rim 32 and out of the opening of the package 10, this feature allows the user to see the insertion of the connector 136 into the funnel 120 and visually inspect the connection. Additionally, after the connection has been made, the user may grasp the distal portion of the funnel 120 extending from the opening of the package 10 to remove the catheter 118 from the package 10, as shown in FIG. 20.

Turning now to FIGS. 7-10, a hydration liner is shown generally at 54. The hydration liner is sized to fit within the tube 20 of the case 12. The liner 54 rests in the tube 20 of the case 20 with the catheter's tube portion 18 (but not the funnel portion) within the liner 54. The liner defines a space between the liner's exterior surface and the case's interior surface within which a hydration mechanism, such as liquid water may reside. This permits hydration of the surface treatment on the catheter.

The liner 54 may be a relatively rigid plastic such as LDPE or HDPE or other relevant materials. The Liner has a generally hollow tube 56. At its upper end there is a seat portion 58 of slightly increased outside diameter compared to the remainder of the tube 56. The seat portion 58 is sized to engage the internal wall of the tube 20. Such engagement is enhanced by a pair of interference ribs 60 formed on the external surface of the seat 58. In addition to the ribs 60, the external surface of the seat 58 has at its top edge a crab claw seal 62. The seal 62 provides a moisture-tight seal against the interior wall of the tube 20. The walls of the liner tube 56 have formed therein one or more passages or windows 64. The windows will be covered with a patch (not shown) of liquid impermeable/vapor permeable material such as, but not limited to, calcium carbonate. The patches will allow passage of water vapor (for hydration of the catheter) but will block passage of liquid water droplets. The patch might be heat sealed around the perimeter of the window.

Figures 11, 12:
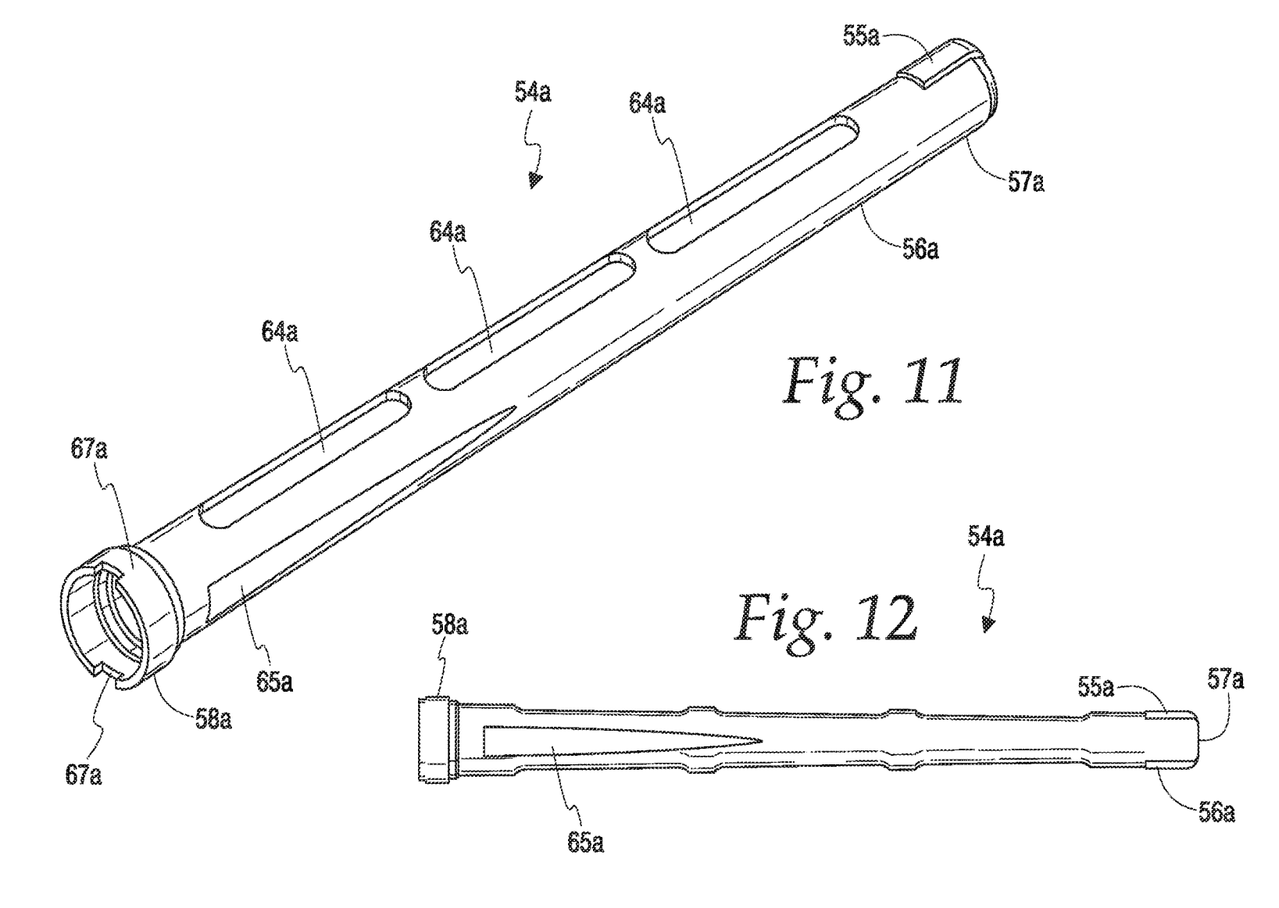
FIG. 11 is a perspective view of another embodiment of a hydration liner that can be used with the packages and assemblies of the present disclosure.
FIG. 12 is a side elevation view of the hydration liner of FIG. 11.

FIGS. 11 and 12 illustrate another embodiment of a hydration liner that is shown generally at 54a. Similar to hydration liner 54, hydration liner 54a is sized to fit within the case shown in FIGS. 1-6 or any other suitable case. The liner 54a rests in the tube of the case with the catheter's tube portion positioned within the liner. The upper seat portion 58a may have a substantially smooth surface that is sized to engage the internal wall of the package case, such as by a friction fit. The upper seat portion may be held in place by fiction fit, heat sealing, adhesive and/or any other suitable manner of attachment. In one embodiment, the substantially smooth surface of the seat portion 58a may, optionally, include a detent or recess that engages, for example, a protruding lip that may be formed on the interior surface of the tube, such as the lip 26 shown in FIG. 6. The friction fit, heat sealing and/or adhesive between the internal wall of the package and the seat portion 58a may provide a moisture-tight seal or the seat portion 58a may include a seal such as crab the claw seal 62 described above. Similar to liner tube 54, the walls of the liner tube 56a may have formed therein one or more passages or windows 64a that may be covered with a liquid impermeable/vapor permeable material.

The liner tubes disclosed herein may have one or more mechanisms or features that assist in aligning the liner tube during the manufacturing process. For example, when the one or more windows 64, 64a are covered with a liquid impermeable/vapor permeable material, the alignment features and mechanisms may be used to orientate or align the liner tube during a process for attaching the liquid impermeable/vapor permeable material to the liner tube. In one embodiment, the alignment features assist in aligning and holding the liner tuber during a heat sealing process for attaching a liquid impermeable/vapor permeable calcium carbonate material to the liner tube. Such aligning mechanisms and features may also be used to transfer and orientate the liner tube along a production line. Furthermore, the case may also include alignment features, which may correspond to the alignment features of the liner tube, that assist in aligning the liner tube and case relative to one another during assembly of the package so that the liner tube is in a desired orientation relative to the case. In one example, the alignment features may include one or more protrusions 55a located at the closed end 57a of the liner tube 56a. Additionally, the alignment features of the liner tube 56a may include flat surfaces located on the sides of liner tube 56a that, optionally, may be tapered. In the illustrated embodiment, liner tube 56a includes a flat, tapered surface 65a. In other examples, the liner tube 56a may include a plurality of flat surfaces. For instance, the liner tube 56a may include flat, tapered surfaces 65a on opposed sides of the tube. Furthermore, the seat 58a of the liner tube 56a may include alignment features that include notches or cutouts 67a. It will be understood that the liner tubes may include one or more of above described alignment features.

This product is helpful as it addresses issues that many intermittent catheter users are experiencing, especially around the areas of hygiene after use, ease of removal of the catheter and the opening of the product. In these criteria the package of the present disclosure is superior to currently available products, especially in discreet female intermittent catheters. For example, a typical intermittent catheter user is a multiple sclerosis sufferer. Multiple sclerosis sufferers have varying levels of dexterity and grip strength which can also vary from day to day in some patients. Having an easy to open package is reassuring that they will always able to void their bladder confidently.

The hygienic re-capture of the catheter into its packaging is also an important feature of the packaging that other catheters do not fully address; with the twist cap concept of the present disclosure the catheter can be safely captured after use without fears of spills. Our catheter funnel, unlike many prior art funnels, is also able to be used with drainage bags made by a variety of manufacturers. It is also noted that the case's opening and closing mechanism is familiar to everyone used to dealing with everyday closures. Further, the amount of the funnel presented to the user makes it easy to grasp.

Among the advantages of the present disclosure are: intuitiveness to open; ease of opening; ease of removal of the catheter from the case; ease of closing of the case after use; discretion and clean to carry after use; and hygienic use.

Figure 13:
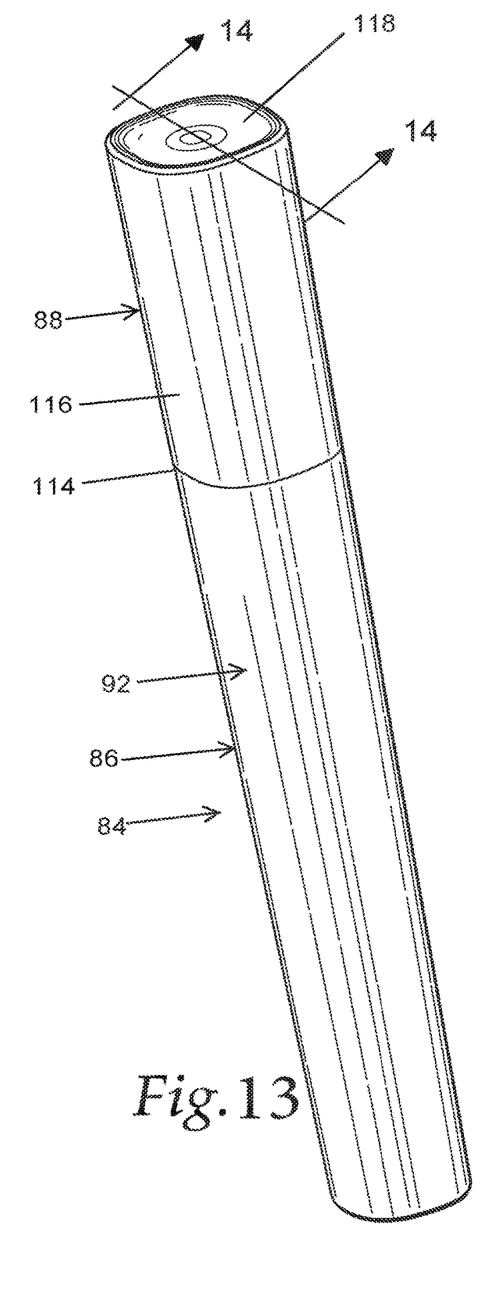
FIG. 13 is a perspective view of a second embodiment of the disclosure, showing a catheter package with a twist-off cap in a closed position.
Figure 14:
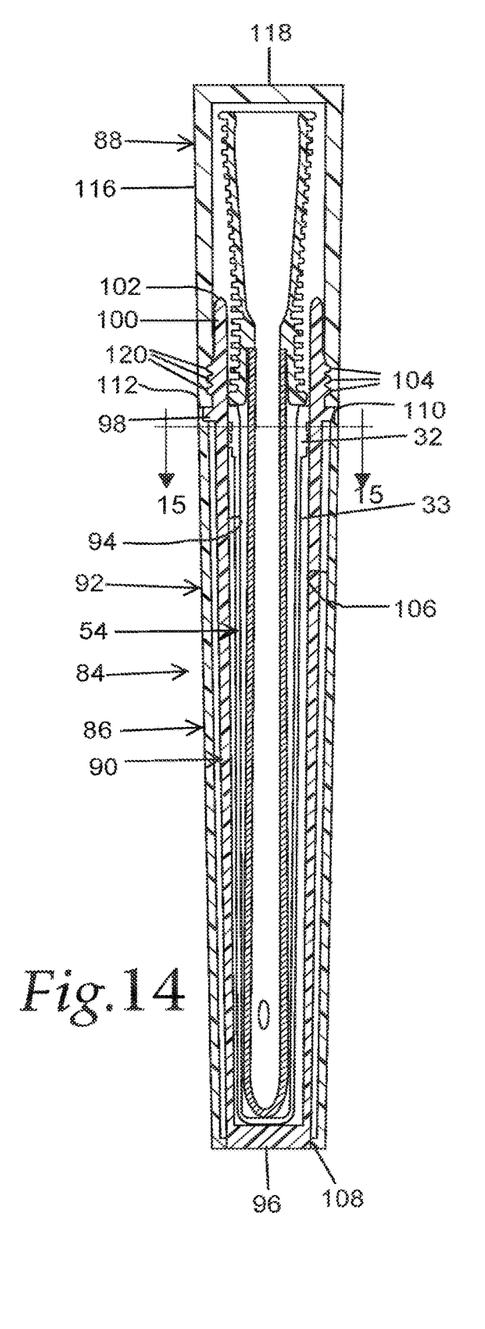
FIG. 14 is a longitudinal section taken along line 14-14 of FIG. 13, with a catheter disposed within the package.
Figure 15:
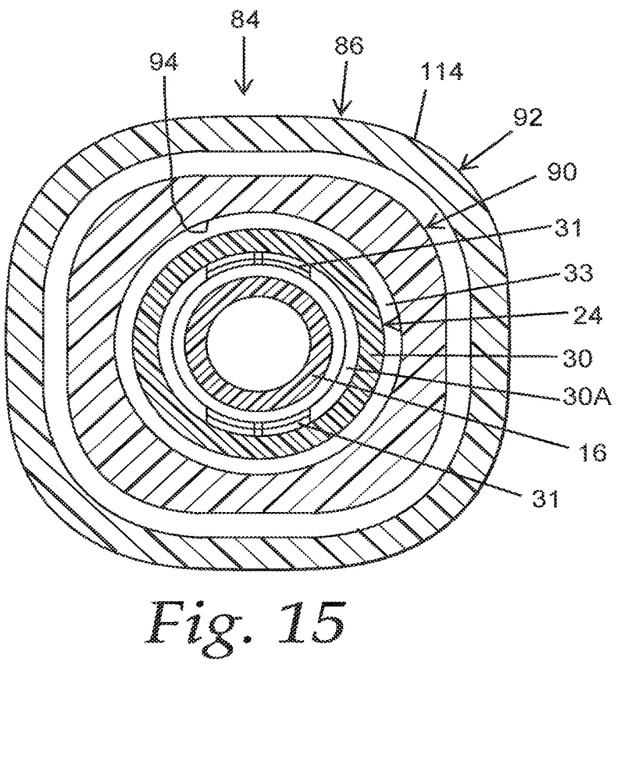
FIG. 15 is a section taken along line 15-15 of FIG. 14.

FIGS. 13-15 illustrate a further alternate embodiment of the catheter package according to the present disclosure. This package, shown generally at 84, includes a container 86 and a cap 88. The cap 88 in this embodiment is a twist cap that is threadably connectable to the container 86 and is selectably movable by a user between a closed position, shown in FIGS. 13 and 14, and an open position (not shown) wherein the cap 88 is removed from the container 86.

The container 86 in this embodiment is a three-part structure including a hydration liner 54, a case 90, and a sleeve 92. Each of these three parts is basically an elongated, hollow tube, open at the top end, with the open top end being selectably openable and closable by the cap 88. The hydration liner 54 fits within the case 90 which in turn fits within the sleeve 92, as seen in FIGS. 14 and 15. The structure and function of the hydration liner 54 is the same as in FIGS. 7-10 so the description of the hydration liner 54 will not be repeated here.

Turning now to the details of the case 90, the case includes a hollow tube 94 which terminates at an end wall 96 that closes the bottom of the tube 94. The tube 94 is shown here with a generally rectangular cross-sectional shape. It will be understood the cross-sectional shape could alternately be cylindrical or otherwise. The upper end of the tube 94 has a radially outwardly extending shoulder 98. Above the shoulder 98 there is a cylindrical ferrule 100. The ferrule terminates at an open end which defines a rim 102. In some respects the ferrule 100 can be considered part of the upper end of the tube 94 except the ferrule is cylindrical, not rectangular. External threads 104 are formed on the external surface of the ferrule 100. The internal surface of the ferrule 100 is engageable with the bottom of the funnel 14 in a press fit while the internal surface of the tube 94 at the location opposite the shoulder 98 engages the seat 32 of the hydration liner 24 in a press fit.

The sleeve 92 is essentially an enlarged version of the case 90 but without a radial shoulder or cylindrical ferrule. As such the sleeve has a hollow tube 106 that terminates at the bottom at an inwardly directed flange 108. The upper end of the tube 106 has a notch 110 adjacent its top land 112. The notch 110 receives the shoulder 98 of the case 90. The top land 112 has an outer contour that is essentially the same as that shown at 114 in FIG. 7.

Details of the cap 88 will now be described. The cap includes a hollow shell which has a longitudinal wall 116 and terminates at a top wall 118 that closes the top of the shell. The longitudinal wall 116 of the shell is shown here with a generally rectangular cross-sectional shape on the exterior surface. It will be understood the external cross-sectional shape could alternately be cylindrical or otherwise so long as it matches the cross-sectional shape of the top land 112 of the sleeve 92. The longitudinal wall 116 of the cap has on its internal surface three helical threads 120. These threads are engageable with the threads 104 on the ferrule.

As best seen in FIG. 13, the matching outer contours of the container 86 and cap 88 provides a smooth, continuous shape for the package 84 as a whole. There are no discontinuities, protrusions or interruptions of any kind in the outside of the package, thereby affording an aesthetically pleasing appearance to the package. For certain users of intermittent catheters this provides an extra measure of comfort, security and discretion.

Figure 16:
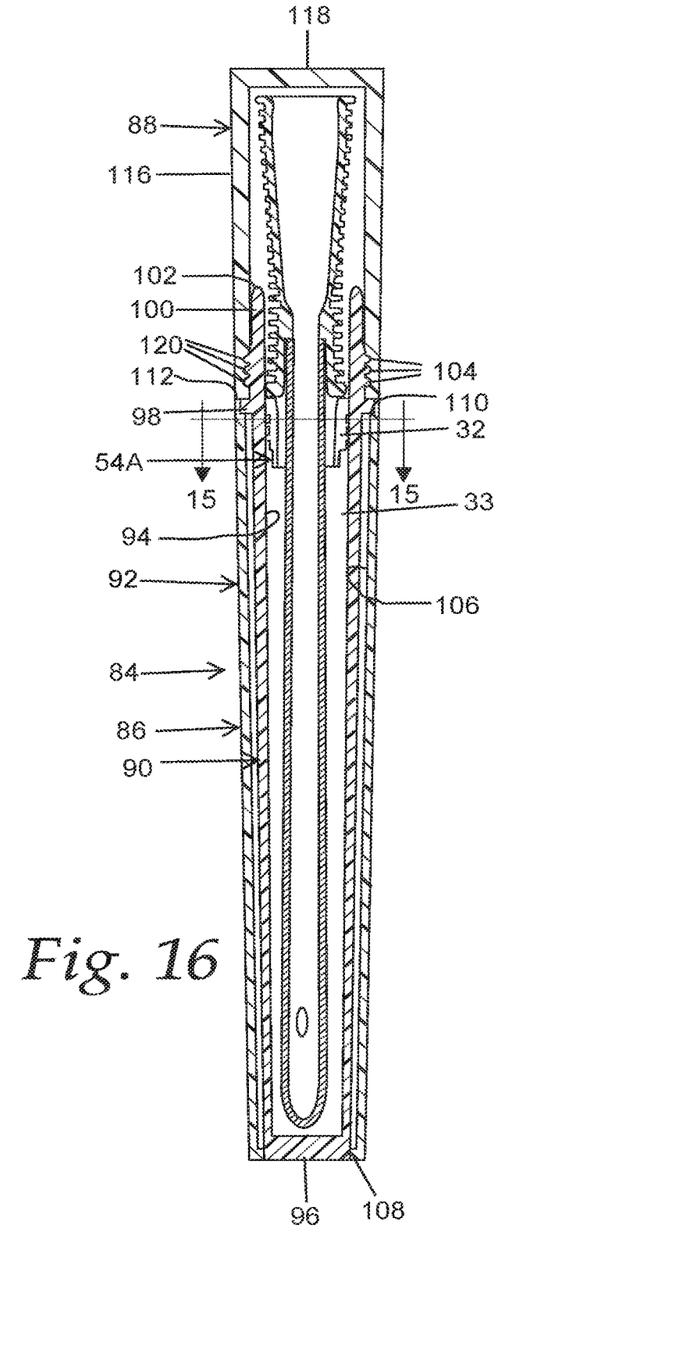
FIG. 16 is a view similar to FIG. 14 showing a further alternate embodiment of a liner.

An alternate version of a liner 54A is shown in FIG. 16. The liner is similar to the liner of FIGS. 7 and 14 except that the length of the hollow tube 56 (shown in FIG. 7) is truncated when compared to the hollow tube 56 of FIG. 7. This truncated version of the liner 54A may be used where direct hydration of the catheter tubing with liquid water is utilized. The upper portion of the seat of the liner 54A will seal against the interior surface of the tube 20. The catheter tubing will seal against the bottom of the funnel. After removal of the catheter if the case is laid on its side the liner 56A will prevent leakage of hydration water out the open top of the case. This is because the inside diameter of liner 54A is small enough to prevent drainage of the small amount of water used for hydration. That is, with the package on its side, there is not enough hydration water to flood the lowermost wall of a horizontally disposed tube to a depth that would leak out through the center of the liner 54A. Thus, the liner 54A serves as a plug to retain hydration water even when the catheter is not in the package.

It should be understood that various changes and modifications to the presently preferred embodiments described herein will be apparent to those skilled in the art. Such changes and modification can be made without departing from the spirit and scope of the invention disclosed herein.

The invention claimed is:

1. A catheter assembly comprising:
   a package including a case comprising a hollow tube and having an open end defining a rim and a cap engageable with the open end of the case and movable between an open and a liquid-tight closed position, each of said case and said cap including threads for releasable engagement with one another;

a hydrophilic coated catheter comprising a catheter tube and a funnel at a distal end of said catheter tube, wherein said catheter tube is contained within said hollow tube of said case and at least a portion of said funnel protrudes above said rim of said case, and wherein the funnel is releasably engaged with an interior surface of the case; and a liquid hydration mechanism for hydrating the hydrophilic coated catheter.

2. The catheter assembly of claim 1 wherein said case further comprises a radially outwardly extending shoulder and a ferrule extending therefrom.

3. The catheter assembly of claim 2 wherein said catheter funnel includes a flange at a bottom end of said funnel and said ferrule includes an internal bead for engagement with said flange.

4. The catheter assembly of claim 1 further comprising a hydration liner disposed within said hollow tube of said case.

5. The catheter assembly of claim 4 wherein said liner has a length that is shorter than said catheter tube for direct hydration of said catheter tube.

6. The catheter assembly of claim 1, wherein the threads on said cap include separate and non-continuous threads.

7. The catheter assembly of claim 1, wherein the cap has an outer contour which matches the outer contour of the case to provide a continuous outer surface of the package at the junction of the cap and case when the cap is in the closed position.

8. The catheter assembly of claim 1, wherein the cap includes a hollow shell with a longitudinal wall.

9. The catheter assembly of claim 8, wherein the longitudinal wall includes a skirt which tapers radially outwardly toward a bottom open end.

10. The catheter assembly of claim 9, wherein the skirt has an inner bead.

11. The catheter assembly of claim 10, wherein said case further comprises a radially outwardly extending shoulder and a ferrule extending therefrom.

12. The catheter assembly of claim 11, wherein the ferrule has an outer bead that interacts with the inner bead of the skirt.

13. The catheter assembly of claim 9, wherein the cap threads are located on an internal wall of the skirt of the cap.

14. A catheter assembly comprising a package including a case comprising a hollow tube and having an open end defining a rim and a cap engageable with the open end of the case and movable between an open and a liquid-tight closed position, each of said case and said cap including threads for releasable engagement with one another;

a hydrophilic coated catheter comprising a catheter tube and a funnel at a distal end of said catheter tube, wherein said catheter tube is contained within said hollow tube of said case and at least a portion of said funnel protrudes above said rim of said case; and wherein the funnel is releasably engaged with an interior surface of the case.

15. The assembly of claim 14 wherein the funnel includes a flange that is releasably engaged with a rib on the interior surface of the case.

16. The assembly of claim 14 wherein a distal portion of the catheter extends axially beyond the rim and is exposed when the cap is in the opened position.

17. The assembly of claim 14, wherein the case further includes a ferrule that terminates at the open end.

18. The assembly of claim 17, wherein the ferrule has an external surface, the external surface including threads formed thereon, the ferrule threads being releasably engageable with an internal surface of the cap.

19. The assembly of claim 18, wherein the internal surface of the cap includes threads formed thereon, the cap threads being releasably engageable with the ferrule threads to permit selectable installation and removal of the cap on the case.

20. The assembly of claim 19, further comprising a first bead formed on the ferrule between the ferrule threads and the opening, and a second bead formed on the cap between the cap threads and a top wall of the cap, the first and second beads cooperating with one another to form a liquid-tight seal between the cap and the case.

\* \* \* \* \*